United States Patent [19]

Nishioka et al.

[11] Patent Number: 5,184,513
[45] Date of Patent: Feb. 9, 1993

[54] AUTOMATIC ULTRASONIC TESTING APPARATUS FOR DETECTING FLAWS OF STRUCTURAL BALLS

[75] Inventors: Shigeo Nishioka, Nagoya; Koji Fushimi, Gifu, both of Japan

[73] Assignee: NGK Insulators, Ltd., Nagoya, Japan

[21] Appl. No.: 588,878

[22] Filed: Sep. 27, 1990

[30] Foreign Application Priority Data

Sep. 29, 1989 [JP] Japan .................. 1-254421

[51] Int. Cl.⁵ ................ G01M 13/04; B25J 15/08
[52] U.S. Cl. ........................ 73/593; 73/618; 901/37; 294/88; 294/104; 294/116
[58] Field of Search ............. 73/593, 644, 618; 209/590, 903, 217; 221/210, 219, 220; 901/37; 294/88, 104, 116

[56] References Cited

U.S. PATENT DOCUMENTS

| | | | |
|---|---|---|---|
| 4,969,361 | 11/1990 | Kawasaki et al. | 73/593 |
| 5,005,417 | 4/1991 | Kawasaki et al. | 73/593 |
| 5,056,368 | 10/1991 | Kawasaki et al. | 73/593 |
| 5,060,517 | 10/1991 | Fushima et al. | 73/593 |

FOREIGN PATENT DOCUMENTS 1464117 11/1966 France.

Primary Examiner—Hezron E. Williams
Assistant Examiner—Michael Brock
Attorney, Agent, or Firm—Shea & Gould

[57] ABSTRACT

An immersion type automatic ultrasonic testing apparatus for detecting flaws of balls comprising a tank for containing a liquid medium of transmitting ultrasonic wave, a ball rotating device for rotating a ball to be tested, an ultrasonic flaw detection device for detecting flaws in the ball while swiveling a probe around the ball rotated by the ball rotating device or rotating the ball spirally by the ball rotating device with or without swiveling the probe, and a ball feeding and removing device for feeding the ball to the position of the ball rotating device and removing the tested ball from the ball rotating device to a predetermined position. The ball feeding device comprises a holding device having an air cylinder and a tip with a pair of holder claws and a pair of side support claws for holding the ball.

5 Claims, 3 Drawing Sheets

FIG.1(a)
FIG.1(b)
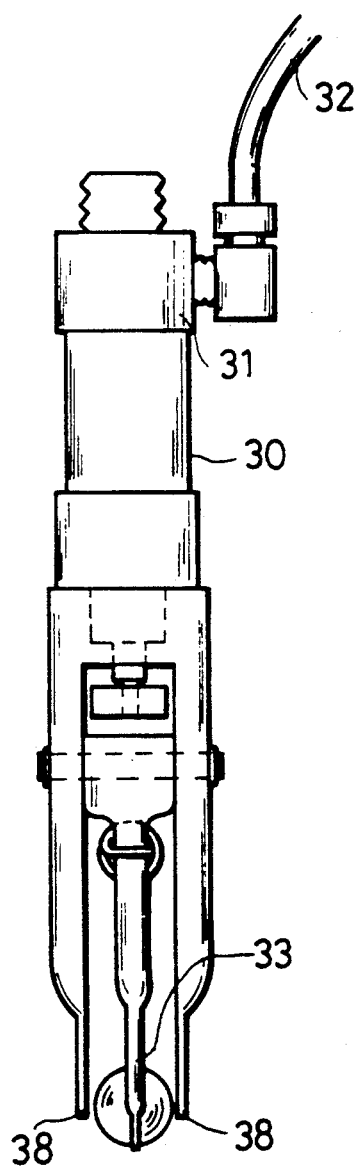
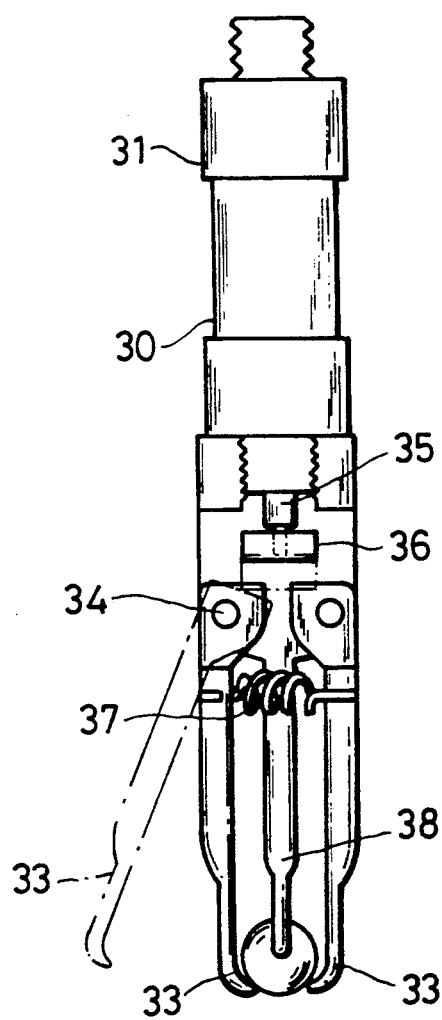

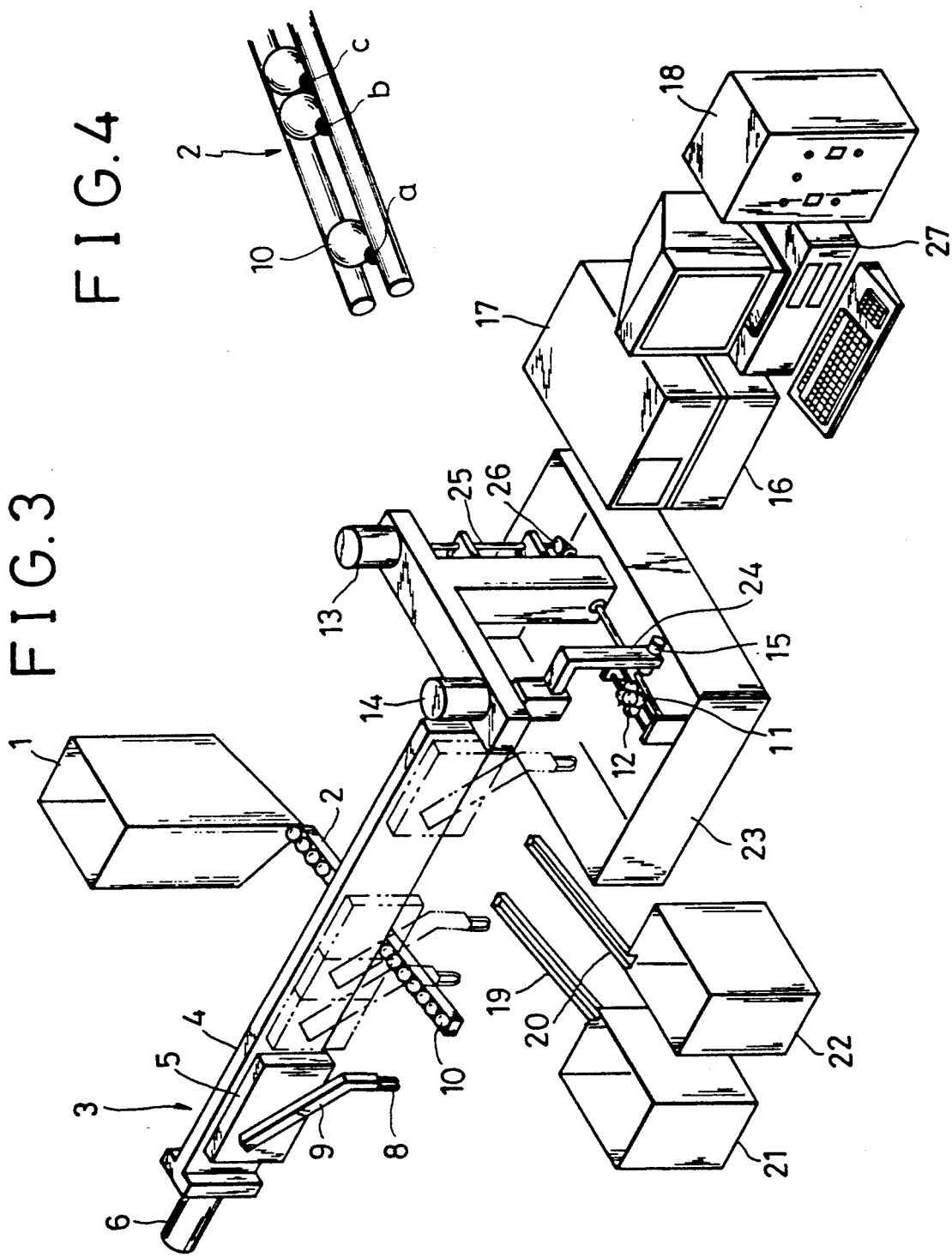

AUTOMATIC ULTRASONIC TESTING APPARATUS FOR DETECTING FLAWS OF STRUCTURAL BALLS

BACKGROUND OF THE INVENTION AND RELATED ART STATEMENT

1. Field of the Invention

This invention relates to an automatic ultrasonic testing apparatus for detecting flaws of structural balls, and more particularly to an automatic ultrasonic testing apparatus for structural balls which is capable of automatic and efficient detection of flaws in the structural balls.

2. Description of the Related Art

Tests on the outer surface and the interior of the structural balls for structural members have hitherto been made by an X-ray testing; by fluorescent penetrate testing or by examining the appearance of the structural balls under a microscope or with the naked eye.

In the X-ray or fluorescent penetrate testing or the inspection of the appearance under a microscope or with the naked eye, however, the object of testing, i.e., the ball structural for structural member is rotated manually and, therefore, much time is required for testing the entire peripheral surface of the ball. In addition, it is doubtful whether the entire peripheral surface of the ball can always be tested completely.

In order to overcome the drawbacks of the conventional testing methods mentioned above, one of the present inventors have previously proposed with other inventors, in U.S. patent application Ser. No. 07/311,041, now U.S. Pat. No. 4,969,361, (identified with Japanese Patent Application Laid-Open (KOKAI) No. 1-219554(1989)), an ultrasonic testing method and apparatus by which the entire peripheral surface of the ball can be tested by placing the ball on drive rollers and rotating the ball.

In the proposal of the ultrasonic testing method and apparatus disclosed in the U.S. Ser. No. 07/311,041 application, however, there is no concrete description of means for feeding the ball onto the drive rollers, only a description of holding the ball by the suction of an air cylinder.

SUMMARY OF THE INVENTION

It is an object of this invention to enhance the total testing efficiency of an ultrasonic testing apparatus through further improvements in the apparatus according to the U.S. patent application Ser. No. 07/311,041.

According to this invention, there is provided an apparatus for automatic ultrasonic testing for detecting flaws of structural balls which comprises a tank for containing a liquid medium capable of transmitting an ultrasonic wave, a ball rotating means for rotating a ball to be tested, an ultrasonic flaw detection means for detecting flaws in the ball, which is while horizontally swiveling a probe around the ball vertically rotated by the ball rotating means; or by rotating the ball spirally by the ball rotating means with or without swiveling the probe; and a ball feeding and removing means for feeding the ball to the position of the ball rotating means and removing the tested ball from the ball rotating means to a predetermined position, the ball feeding and removing means comprising a holding means having an air cylinder and a tip with a pair of holder claws and a pair of side support claws for holding the ball.

The above and other objects, features and advantages of this invention will become apparent from the following description and appended claims, taken in conjunction with the accompanying drawings which show by way of example some preferred embodiments of the invention.

BRIEF DESCRIPTION OF THE DRAWINGS

FIGS. 1 illustrate one embodiment of a ball feeding means used in an automatic ultrasonic testing apparatus according to this invention, in which FIG. 1(a) is a front view and FIG. 1(b) a side view;

FIGS. 2 illustrate one embodiment of the relationship between a ball rotating means and a ball feeding and removing means, in which

FIG. 3 is a perspective view showing the total arrangement of one embodiment of an automatic ultrasonic testing apparatus for detecting flaws of structural balls in which the ball feeding and removing means is incorporated; and FIG. 4 is a perspective view of a tip portion of an untested-ball supply chute.

DETAILED DESCRIPTION OF THE PREFERRED EMBODIMENTS

Figure 2A:
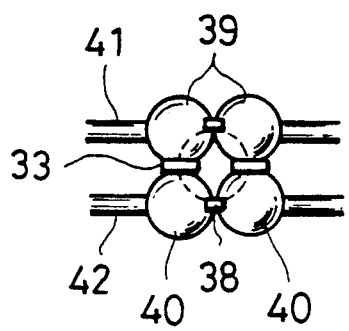
FIG. 2(a) is an illustrative plan view and FIG. 2(b) is an illustrative side view.

The automatic ultrasonic testing apparatus according to this invention comprises, a ball rotating means, an ultrasonic testing means and a ball feeding and removing means, the ball feeding and removing means including a holding means having an air cylinder and a tip with a pair of holder claws and a pair of side support claws for supporting the ball.

After the ball is held by the pair of holder claws and the pair of side support claws of the holding means, the ball is conveyed to rotating rollers of the ball rotating means and is lowered to a position just above the rotating rollers. The rollers are immersed in a liquid medium for transmitting an ultrasonic wave, for example, water, oil, etc. At this moment, each tip of the pair of the holder claws is located between two pairs of the rollers, whereas each tip of the pair of the side support claws is located directly above the rollers. Next, only the holder claws are opened to the left and right, to place the ball on the rollers, and the ball holding portion is raised away from the ball. Then, flaw detection is carried out while the probe is swiveled around the ball by the ultrasonic flaw detection means or while the ball is rotated spirally and the probe is maintained stationary or swiveled, if necessary. In conducting the flaw detection, an ultrasonic wave is sent from the probe toward the ball, an ultrasonic echo reflected back from the ball is received, and the waveform of the echo signal is observed on an ultrasonic flaw detector connected to the probe, thereby detecting flaws in the ball.

After the flaw detection for the ball is finished, the ball holding portion is lowered, each tip of the holder claws located between two pairs of rollers is closed to hold the ball, and the ball holding portion is moved upward. In this case, the side support claws prevent the ball from dropping. The ball is conveyed to a predetermined place, then a new ball to be tested is gripped and fed onto the ball rotating means, to be subjected to flaw detection. According to the ball feeding and removing means of this invention, flaw detection for a predetermined number of balls to be tested is automatically, smooth and speedily carried out, because the balls can be placed or removed from the ball rotating rollers immersed in the aforementioned liquid medium without adjusting the level of the medium, if compared with the prior arts which needed to make the level of the medium lower.

The ball as the material to be tested, namely, the object of the ultrasonic testing according to this invention is a ball used for a bearing member, a wear-resistant member or a sliding member. These types of balls, whether made of ceramic or metal, can be used as the object of the ultrasonic testing of this invention, without any particular restrictions. However, ceramic balls are particularly effective for use as the object of the ultrasonic testing according to this invention, because the reliability of the ceramic balls is heavily dependent on the accurate detection of minute flaws in the surface and the sub-surface of the balls.

In regard to ceramic balls, those ceramic balls which comprise silicon nitride, silicon carbide, zirconia or alumina are preferably used, in view of the high strength and high hardness requirements of bearing members, wear-resistant members, sliding members, etc.

This invention will now be described in detail below while referring to the embodiments shown in the drawings; it is to be understood, however, that the scope of the invention is not limited to the embodiments.

FIG. 1 illustrate one embodiment of a ball feeding and removing mechanism used in an automatic ultrasonic testing apparatus according to this invention, in which FIG. 1(a) is a front view and FIG. 1(b) a side view.

In FIGS. 1, denoted by 30 is a single acting type air cylinder, which has a rear port 31 to be supplied with air from a compressor or the like (not shown) via an air hose 32, which is a transmitter of an air pressure.

A pair of side support claws 38 is fitted to the tip of the air cylinder 30, and a pair of holder claws 33 is fitted to the side support claws 38 with shafts 34, and the pair of holder claws 33 which are opened and closed by a lever action with the shafts 34 as fulcra. The ball is held and released by the closing and opening of the holder claws. The pair of side support claws 38 is maintained stationary, functioning only to prevent the ball from falling off. Coil spring 37 fitted between holder claws 33 in order to provide a bias force during the claws together.

With air supplied to the rear port 31 of the single acting type air cylinder 30, an air cylinder rod 35 is lowered, and a push plate 36 attached to rod 35 for opening the holder claws 33 presses against a rear portion of each of the holder claws 33.

The pair of holder claws 33 thus pressed is turned about the respective shafts 34, against the bias force of a coil spring 37 fitted between the holder claws 33, so that the tips of the claws 33 are opened outward. In this condition, the ball is placed at a lower portion of a space between the holder claws 33, and the air in the air cylinder 30 is removed, whereupon the holder claws 33 are closed by the force of the coil spring 37 to hold the ball. In this case, when the side support claws 38 fitted to the tip of the air cylinder 30 and disposed in a rectangular positional relationship with the holder claws 33 are set with a spacing therebetween being slightly greater than the diameter of the ball, the ball is prevented from slipping off the holder claws 33.

Figure 2B:
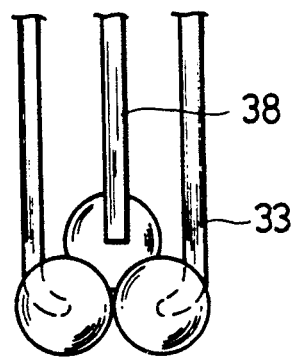

After the ball is held by the holder claws 33 and the air cylinder 30 is moved to a position just above the ball rotating device immersed in water as the liquid medium of transmitting ultrasonic wave contained in a tank 23, the air cylinder rod 35 is again lowered and the holder claws 33 are opened to place the ball on the ball rotating device. As shown in FIGS. 2(a) and 2(b), the holder claws 33 are each located between two shafts 41 and 42 and two pairs of rotating rollers 39 and 40 fitted to the shafts 41 and 42 respectively, whereas the tips of the side support claws 38 are located directly above the rollers 39 and 40. Next, the holder claws 33 are opened in the same manner as above, thereby placing the ball on the ball rotating device comprising the rotating rollers 39 and 40, and the air cylinder 30 is raised.

On the inside of the holder claws 33 and the side support claws 38, there is a sufficient space for the ball to move vertically. At the time of placing the ball on the rotating rollers 39 and 40, therefore, no irrational forces are exerted on the rollers 39 and 40, and it is unnecessary to enhance the accuracy of the position of the ball relative to other members.

FIG. 3 is a perspective view showing the total arrangement, of one embodiment of an automatic ultrasonic testing apparatus for detecting flaws of balls which incorporates the ball feeding and removing means.

In FIG. 3, denoted by 1, is a container for supplying untested balls. The untested balls 10 placed in the container 1 are aligned along an untested-ball supply chute 2 sloped down toward the tip thereof. As shown in FIG. 4, stoppers a, b and c for stopping the ball are provided at a tip portion of the chute 2. The stopper a is set stationary, for stopping the ball at a predetermined position. On the other hand, the stoppers b and c are movable, and function to feed out the balls to the predetermined position, one ball at a time. Denoted by 3 is a ball feeding device, which comprises a feed carriage 5 capable of moving along a feed rail 4. The carriage 5 is capable of being moved along the feed rail 4 to an arbitrary position by a feeding drive motor 6 and be stopped in the arbitrary position. The carriage 5 is equipped with an air cylinder 9 shown in FIG. 1 (in FIG. 1, denoted by 30).

At the start of the ultrasonic testing for detecting flaws in a ball, the feed carriage 5 is located in a position corresponding to the untested-ball supply chute 2, and the holder claws 8 (in FIG. 1, denoted by 33) of the air cylinder 9 are in an opened condition. Next, the air cylinder 9 is lowered, and an untested ball 10 disposed at the tip of the chute 2 is held by the holder claws 8. After the ball 10 is thus held, the air cylinder 9 is moved upward, and the carriage 5 is moved to a position corresponding to rollers 11 (in FIG. 2, denoted by 39 and 40) for rotating the ball under test, and is stopped at that position. The air cylinder 9 is then lowered. When the untested ball 10 is brought to the position for the ball 12 on the rotating rollers 11, the holder claws 8 are opened to place the untested ball 10 on the rollers 11 immersed in water contained in the tank 23, and the air cylinder 9 is retracted.

Next, a motor 13 for rotating the ball under test is operated to rotate the rollers 11, thereby vertically or spirally rotating the ball 12 under test. Simultaneously with the rotation of the ball 12, a probe swiveling motor 14 is rotated so that a probe 15 immersed in water is horizontally swiveled 180° by a probe swiveling arm 24 when vertically or spirally rotating the ball 12, or the probe swiveling motor 14 is not operated so that the probe 15 is fixed without being swiveled when spirally rotating the ball 12. In FIG. 3, numeral 25 denotes a shaft for transmitting a rotating force for the ball under test, and numeral 26 denotes a bevel gearing for transmitting the rotating force. The probe 15 is connected to an ultrasonic flaw detector 16, and the test for detecting internal flaws in the ball 12 is carried out over the entire periphery of the ball. When a flaw is present in the ball, a flaw waveform of the echo signal is observed on an oscilloscope 17 of the ultrasonic flaw detector 16, and a flaw signal is sent to a mechanical drive portion control panel 18. A computer 27 is provided for controlling the ultrasonic flaw detector 16 and analyzing the flaw detection data.

After the ultrasonic test on the entire periphery of the ball 12 is finished, the air cylinder 9 is lowered to hold the ball 12 in water by the holder claws 8. With the ball 12 thus held, the air cylinder 9 is retracted, and the feed carriage 5 is moved to and stopped in either a position corresponding to an accepted-ball discharge chute 19 or a position corresponding to a rejected-ball discharge chute 20, according to the absence or presence of the flaw signal. On the upper side of either one of the discharge chutes, the air cylinder 9 is lowered, and the holder claws 8 are opened to drop the ball. The ball rolls down the discharge chute, to be contained into an accepted-ball receiver 21 or a rejected-ball receiver 22.

After the ball is thus dropped, the air cylinder 9 is retracted, and the feed carriage 5 is moved to the initial position corresponding to the untested-ball supply chute 2 and stopped in that position.

Thereafter, the above process is repeated, whereby the ultrasonic test for detecting flaws of the balls in the aforementioned liquid medium can be carried out automatically to separate accepted balls and rejected balls from each other.

Solenoid valves for operating the air cylinder and for a suction cup, limit switches for positioning mechanical drive portions, such as the feeding device, and the like, which are not shown, are controlled appropriately by the mechanical drive portion control panel 18.

As has been described above, the automatic ultrasonic testing apparatus for detecting flaws of balls according to this invention is capable of performing an automatic and speedy detecting flaws test on the balls, completely over the entire periphery of each ball.

What is claimed is:

1. An immersion type automatic ultrasonic testing apparatus for detecting flaws of a structural ball which comprises:
    a tank for containing a liquid medium capable of transmitting an ultrasonic wave,
    a ball rotating means for rotating a ball to be tested,
    an ultrasonic flaw detection means for detecting flaws in the ball while swiveling a probe around the ball rotated by the ball rotating means or rotating the ball spirally by the ball rotating means with or without swiveling the probe, and
    a feeding and removing means for feeding the ball to the position of the ball rotating means and removing the tested ball from the ball rotating means to a predetermined position, the feeding and removing means comprising a holding means having an air cylinder and a tip with a pair of holder claws and a pair of side support claws, wherein said air cylinder actuates said pair of holder claws for holding the ball.

2. An apparatus according to claim 1, wherein each tip of the holder claws is adjusted to be located between two pairs of rotating rollers of the rotating means which the ball is placed onto or removed from.

3. An apparatus according to claim 1 or 2, further comprising a biasing means for biasing said pair of holder claws in a closed position, wherein the pair of side support claws is fitted to the tip of the holding means, and each of the holder claws is pivotally attached to the pair of side support claws with a shaft.

4. An apparatus according to claim 3, wherein the pair of holder claws can turn around the shaft and open by being pressed at the rear portion by the air cylinder pressure.

5. An apparatus according to claim 3, wherein the biasing means comprises a coil spring attached between the pair of holder claws.

* * * * *